(12) United States Patent
Von Matt et al.

(10) Patent No.: US 7,820,672 B2
(45) Date of Patent: Oct. 26, 2010

(54) INDOLYLMALEIMIDE DERIVATIVES

(75) Inventors: Peter Von Matt, Biel-Benken (CH); Jürgen Wagner, Bottmingen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/542,175

(22) PCT Filed: Feb. 12, 2004

(86) PCT No.: PCT/EP2004/001323

§ 371 (c)(1),
(2), (4) Date: Jul. 14, 2005

(87) PCT Pub. No.: WO2004/072062

PCT Pub. Date: Aug. 26, 2004

(65) Prior Publication Data

US 2006/0058356 A1    Mar. 16, 2006

(30) Foreign Application Priority Data

Feb. 13, 2003    (GB) ................................. 0303319.8

(51) Int. Cl.
*A61K 31/497*    (2006.01)
*A61K 31/4439*   (2006.01)
*A61K 31/4015*   (2006.01)
*A61K 31/404*    (2006.01)
*C07D 403/14*    (2006.01)

(52) U.S. Cl. .................. 514/253.09; 514/339; 514/414; 544/364; 546/277.4; 548/466; 548/548

(58) Field of Classification Search ................ 548/466, 548/548; 514/253.09, 339, 414; 544/364; 546/277.4
See application file for complete search history.

(56) References Cited

U.S. PATENT DOCUMENTS 5,057,614 A * 10/1991 Davis et al. ................. 548/466
5,405,864 A    4/1995 Broka ......................... 514/415
5,559,228 A    9/1996 Gillig et al. ................. 540/460

FOREIGN PATENT DOCUMENTS

| | | |
|---|---|---|
| DE | 40 05 970 | 8/1991 |
| EP | 0 328 026 | 8/1989 |
| EP | 0 540 956 | 5/1993 |
| FR | 2 772 266 | 6/1999 |
| FR | 2 799 200 | 4/2001 |
| JP | 63-24245 | 2/1988 |
| JP | 6-161024 | 6/1994 |
| JP | 9-61647 | 3/1997 |
| JP | 2002-285146 | 10/2002 |
| WO | 93/18765 | 9/1993 |
| WO | 00/21927 | 4/2000 |
| WO | 00/38675 | 7/2000 |
| WO | 01/30331 | 5/2001 |
| WO | 01/46178 | 6/2001 |
| WO | 01/85685 | 11/2001 |
| WO | 02/10158 | 2/2002 |
| WO | 02/38561 | 5/2002 |
| WO | WO 0238561 A1 * | 5/2002 |
| WO | 02/078679 | 10/2002 |
| WO | 03/076398 | 9/2003 |

OTHER PUBLICATIONS

Patani et al. "Bioisosterism: A Rational Approach in Drug Design" Chemical Reviews, 1996, vol. 96, pp. 3147-3176.*
McMurry, John "Organic Chemistry—Fourth Edition" Brooks/Cole Publishing Company, 1996, p. 553.*

* cited by examiner

*Primary Examiner*—Joseph R Kosack
(74) *Attorney, Agent, or Firm*—Hoxie & Associates LLC

(57) ABSTRACT

The compounds are indolylmaleimide derivatives comprising either a substituted pyridyl or indolyl residue. The compounds have interesting pharmaceutical properties, e.g. in the treatment and/or prevention of T-cell mediated acute or chronic inflammatory diseases or disorders, autoimmune diseases, or acute or chronic transplant rejection.

9 Claims, No Drawings

INDOLYLMALEIMIDE DERIVATIVES

The present invention relates to indolylmaleimide derivatives, process for their production and pharmaceutical compositions containing them.

More particularly the present invention provides a compound of formula I

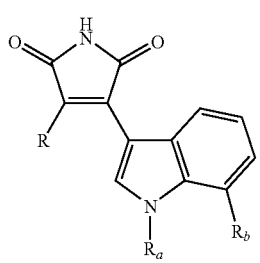

wherein $R_a$ is H; $C_{1-4}$alkyl; or $C_{1-4}$alkyl substituted by OH, $NH_2$, $NHC_{1-4}$alkyl or $N(di-C_{1-4}alkyl)_2$;

$R_b$ is H; halogen; $C_{1-6}$alkyl; or $C_{1-6}$alkoxy, and

R is a radical of formula (a) or (b)

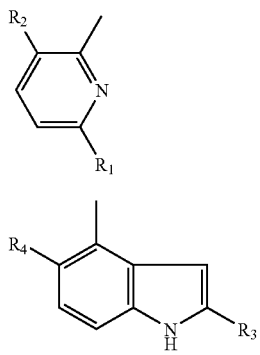

wherein
  each of $R_1$ and $R_3$ is a heterocyclic residue; or a radical of formula α

—X—$R_c$—Y       (α)

wherein X is a direct bond, O, S or $NR_{11}$ wherein $R_{11}$ is H or $C_{1-4}$alkyl,
  $R_c$ is $C_{1-4}$alkylene or $C_{1-4}$alkylene wherein one $CH_2$ is replaced by $CR_xR_y$ wherein one of $R_x$ and $R_y$ is H and the other is $CH_3$, each of $R_x$ and $R_y$ is $CH_3$ or $R_x$ and $R_y$ form together —$CH_2$—$CH_2$—,
  Y is bound to the terminal carbon atom and is selected from OH, —$NR_{12}R_{13}$ wherein each of $R_{12}$ and $R_{13}$, independently, is H, $C_{3-6}$cycloalkyl, $C_{3-6}$cycloalkyl-$C_{1-4}$alkyl, aryl, aryl-$C_{1-4}$alkyl, heteroaryl-$C_{1-4}$alkyl, $C_{2-6}$alkenyl or $C_{1-4}$alkyl optionally substituted on the terminal carbon atom by OH, halogen, $C_{1-4}$alkoxy or —$NR_{14}R_{15}$ wherein each of $R_{14}$ and $R_{15}$, independently, is H, $C_{1-4}$alkyl, $C_{3-6}$cycloalkyl, $C_{3-6}$cycloalkyl-$C_{1-4}$alkyl, aryl-$C_{1-4}$alkyl, or $R_{12}$ and $R_{13}$ form together with the nitrogen atom to which they are bound a heterocyclic residue; and
  each of $R_2$ and $R_4$, independently, is H; halogen; $C_{1-4}$alkyl; $C_{1-4}$alkoxy; $CF_3$; nitrile; nitro or amino.

Any alkyl or alkyl moiety in e.g. alkoxy may be linear or branched. Halogen may be F, Cl, Br or I, preferably F or Cl. Any aryl may be phenyl or naphthyl, preferably phenyl. Heteroaryl may be a 5 to 8 membered aromatic ring comprising 1 to 4 heteroatoms selected from N, O and S, e.g. pyridyl or pyrimidyl.

By heterocyclic residue as $R_1$ or $R_3$ is meant a three to eight, preferably five to eight, membered saturated, unsaturated or aromatic heterocyclic ring comprising 1 or 2 heteroatoms, preferably selected from N, O and S, and optionally substituted.

By heterocyclic residue as Y is meant a three to eight, preferably five to eight, membered saturated, unsaturated or aromatic heterocyclic ring comprising a nitrogen as heteroatom and optionally a second heteroatom, preferably selected from N, O and S, and optionally substituted.

Suitable examples for $R_1$, $R_3$ or Y include e.g. pyridyl, e.g. 3- or 4-pyridyl, piperidyl, e.g. piperidin-1-yl, 3- or 4-piperidyl, homopiperidyl, piperazinyl, homopiperazinyl, imidazolyl, imidazolidinyl, pyrrolyl, pyrrolidinyl or morpholin-4-yl, optionally substituted, e.g. mono- or polysubstituted. When the heterocyclic residue is substituted, this may be on one or more ring carbon atoms and/or on a ring nitrogen atom when present. Examples of a substituent on a ring carbon atom include e.g. $C_{1-4}$alkyl e.g. $CH_3$; $C_{3-6}$cycloalkyl e.g. cyclopropyl, optionally further substituted by $C_{1-4}$alkyl;

wherein p is 1, 2 or 3, preferably 1; $CF_3$; halogen; $NH_2$; —$CH_2$—$NR_{16}R_{17}$ wherein each of $R_{16}$ and $R_{17}$, independently, is H, $C_{1-4}$alkyl, or $R_{16}$ and $R_{17}$ form together with the nitrogen atom to which they are bound a heterocyclic residue or a heteroaryl; —$CH_2$—OH; —$CH_2$—O—$C_{1-4}$alkyl; —$CH_2$-halogen; or —$CH_2$—$CH_2$-halogen. Examples of a substituent on a ring nitrogen atom are e.g. $C_{1-6}$alkyl; acyl, e.g. $R'_x$—CO wherein $R'_x$ is H, $C_{1-6}$alkyl or phenyl optionally substituted by $C_{1-4}$alkyl, $C_{1-4}$alkoxy or amino, e.g. formyl; $C_{3-6}$cycloalkyl; $C_{3-6}$cycloalkyl-$C_{1-4}$alkyl; phenyl; phenyl-$C_{1-4}$alkyl e.g. benzyl; a heterocyclic residue, e.g. as disclosed above, e.g. an aromatic heterocyclic residue comprising 1 or 2 nitrogen atoms; or a residue of formula β

—$R_{18}$—Y'       (β)

wherein $R_{18}$ is $C_{1-4}$alkylene or $C_{2-4}$alkylene interrupted by O and Y' is OH, $NH_2$, $NH(C_{1-4}alkyl)$ or $N(C_{1-4}alkyl)_2$. $C_{2-4}$alkylene interrupted by O may be e.g. —$CH_2$—$CH_2$—O—$CH_2CH_2$—.

When the substituent on a cyclic nitrogen is a heterocyclic residue, it may be a five or six membered saturated, unsaturated or aromatic heterocyclic ring comprising 1 or 2 heteroatoms, preferably selected from N, O and S. Examples include e.g. 3- or 4-pyridyl, piperidyl, e.g. piperidin-1-yl, 3- or 4-piperidyl, homopiperidyl, piperazinyl, homopiperazinyl, pyrimidinyl, morpholin-4-yl, imidazolyl, imidazolidinyl, pyrrolyl or pyrrolidinyl.

Further examples of heterocyclic residue as $R_1$, $R_3$ or Y include e.g. a residue of formula (γ)

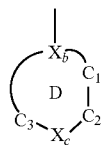

wherein
the ring D is a 5, 6 or 7 membered saturated, unsaturated or aromatic ring;
$X_b$ is —N=, —C= or —CH—;

$X_c$ is —N=, —NR$_f$—, —CR$_f'$= or —CHR$_f'$— wherein R$_f$ is a substituent as indicated above for a ring nitrogen atom, and R$_f'$ is a substituent as indicated above for a ring carbon atom;

the bond between $C_1$ and $C_2$ is either saturated or unsaturated;

each of $C_1$ and $C_2$, independently, is a carbon atom which is optionally substituted by one or two substituents selected among those indicated above for a ring carbon atom; and the line between $C_3$ and $X_b$ and between $C_1$ and $X_b$, respectively, represents the number of carbon atoms as required to obtain a 5, 6 or 7 membered ring D, whereby when Y is a residue of formula (γ) at least one of $X_b$ and $X_c$ is —N=.

A preferred residue of formula (γ) is one wherein the ring D forms a 1,4-piperazinyl ring optionally C- and/or N-substituted as indicated.

Representative examples of a residue of formula (γ) are e.g. 3- or 4-pyridyl; piperidin-1-yl; 1-N—($C_{1-4}$alkyl)- or -(ω-hydroxy-$C_{1-4}$alkyl)-3-piperidyl; morpholin-4-yl; imidazolyl; pyrrolidinyl; 1-piperazinyl; 2-$C_{1-4}$alkyl- or —$C_{3-6}$cycloalkyl-1-piperazinyl; 3-$C_{1-4}$alkyl- or —$C_{3-6}$cycloalkyl-1-piperazinyl; 2,2- or 3,5- or 2,5- or 2,6-di($C_{1-4}$alkyl)-1-piperazinyl; 3,4,5-tri-($C_{1-4}$alkyl)-1-piperazinyl; 4-N-($C_{1-4}$alkyl)- or -(ω-hydroxy-$C_{1-4}$alkyl)- or -(ω-dimethylamino-$C_{1-4}$alkyl)-1-piperazinyl; 4-N-pyridin-4-yl-1-piperazinyl; 4-N-phenyl- or —$C_{3-6}$cycloalkyl-1-piperazinyl; 4-N-($C_{1-4}$alkyl)- or -(ω-hydroxy-$C_{1-4}$alkyl)-3-$C_{1-4}$alkyl- or -3,3-di($C_{1-4}$alkyl)-1-piperazinyl; 4-N-(1-$C_{1-4}$alkyl-$C_{3-6}$cycloalkyl)-1-piperazinyl; 4-N-formyl-1-piperazinyl; 4-N-pyrimidin-2-yl-1-piperazinyl; or 4-N-$C_{1-4}$alkyl-1-homopiperazinyl.

In the radical of formula (b), $R_3$ is preferably a residue of formula (α) wherein X is a direct bond and $R_c$ is —$CH_2$—. Preferably Y is —$NR_{12}R_{13}$. Preferably each of $R_{12}$ and $R_{13}$ have a significance other than forming together with the nitrogen atom to which they are attached a heterocyclic residue.

When $R_a$ is substituted $C_{1-4}$alkyl, the substituent is preferably on the terminal carbon atom.

In the compounds of formula I, the following significances are preferred individually or in any sub-combination:

1. $R_a$ is H, methyl, ethyl, or isopropyl;
2. $R_b$ is H, Cl, methyl or ethyl;
3. $R_1$ is a heterocyclic residue, e.g. a piperazinyl, optionally substituted on a ring nitrogen or on a ring carbon, e.g. 4-methyl-piperazin-1-yl, or 4,7-diaza-spiro[2.5]oct-7-yl; or a radical of formula (α) wherein X is a direct bond, $R_c$ is $CH_2$ and Y is —$NR_{12}R_{13}$ wherein each of $R_{12}$ and $R_{13}$, independently, is H, $C_{3-6}$cycloalkyl-$C_{1-4}$alkyl, $C_{2-6}$alkenyl or $C_{1-4}$alkyl optionally substituted on the terminal carbon atom by OH, halogen, $C_{1-4}$alkoxy or —$NR_{14}R_{15}$ wherein each of $R_{14}$ and $R_{15}$, independently, is H or $C_{1-4}$alkyl; or $R_{12}$ and $R_{13}$ form together with the nitrogen atom to which they are bound a heterocyclic residue e.g. a piperazinyl; or
4. $R_2$ and/or $R_4$ is H; $CH_3$; Cl, F; $CF_3$; nitro or nitrile.

The compounds of formula I may exist in free form or in salt form, e.g. addition salts with e.g. organic or inorganic acids, for example, hydrochloric acid, acetic acid or trifluoroacetic acid.

It will be appreciated that the compounds of formula I may exist in the form of optical isomers, racemates or diastereoisomers. For example, a ring carbon atom bearing a substituent in the position 3 of the piperazinyl residue is asymmetric and may have the D- or L-configuration. It is to be understood that the present invention embraces all enantiomers and their mixtures. Similar considerations apply in relation to starting materials exhibiting asymmetric carbon atoms as mentioned.

The present invention also includes a process for the preparation of a compound of formula I which process comprises reacting a compound of formula II

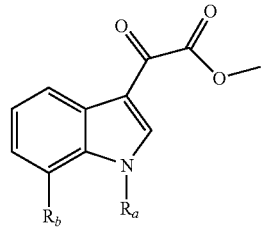

(II)

wherein $R_a$ and $R_b$ are as defined above,
with a compound of formula III

R—$CH_2$—CO—$NH_2$  (III)

wherein R is as defined above, and, where required, converting the resulting compound of formula I obtained in free form to a salt form or vice versa, as appropriate.

The process may conveniently be effected in the presence of a strong base, e.g. t-BuOK, e.g. as disclosed in WO02/38561 or WO 03/08259.

Compounds of formula II and III may be prepared in accordance with known methods, e.g. as disclosed in WO02/38561.

Insofar as the production of the starting materials is not particularly described, the compounds are known or may be prepared analogously to methods known in the art or as described hereafter.

The following examples are illustrative of the invention.

RT=room temperature

DMF=dimethylformamide

THF=tetrahydrofuran

FCC=flash column chromatography

TLC=thin layer chromatography

DBU=1,8-diazabicyclo[5,4.0]undec-7-ene

EtOAc=ethyl acetate

EXAMPLE 1

3-(1H-Indol-3-yl)-4-[6-(4-methyl-piperazin-1-yl)-3-tifluoromethyl-pyridin-2-yl]-pyrrole-2,5-dione

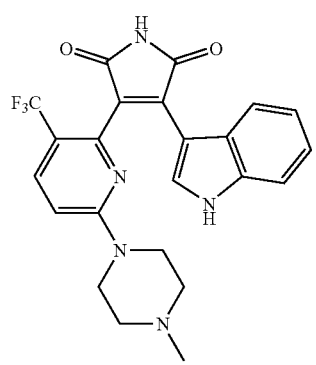

2-[6-(4-Methyl-piperazin-1-yl)-3-trifluoromethyl-pyridin-2-yl]-acetamide (60 mg, 0.132 mmol) and (1H-Indol-3-yl)-oxo-acetic acid methyl ester (40 mg, 0.199 mmol) are azeotroped twice are dry THF and then dissolved in dry THF (2 ml). A solution of 1.0 M KOtBu in THF (0.73 ml) is added dropwise over 2 minutes at RT. The reaction mixture is warmed to 50° C. for 1 hour, after which TLC analysis indicates complete conversion of starting materials. The reaction is quenched by the addition of water (5 ml). The mixture is diluted with EtOAc and washed twice with saturated aq. NH$_4$Cl. The aqueous layers are backextracted twice with EtOAc. The combined organic layers are dried over Na$_2$SO$_4$ and the solvent is evaporated. The residue is purified by FCC (EtOAc/AcOH/H$_2$O 800:55:45 to 750:83:68 to 700:110:90 to 600:150:150) to afford the title compound as its acetate salt. After azeotroping with MeOH/toluene, the product is obtained as its acetate—methanol complex. $^1$H NMR (DMSO, 400 MHz) δ 2.10 (s, 3H), 2.10-2.22 (m, 4H), 3.47-3.52 (m, 4H), 6.58 (d, J=8.9 Hz, 1H), 6.73-6.76 (m, 1H), 7.02 (d, J=10.0 Hz, 1H), 7.04-7.08 (m, 1H), 7.40 (d, J=9.4 Hz, 1H), 7.84 (d, J=10.0, 1H), 8.03 (s, 1H); ES-MS: 456.5 [M+H]$^+$.

2-[6-(4-Methyl-piperazin-1-yl)-3-trifluoromethyl-pyridin-2-yl]-acetamide used as starting material may be prepared as follows:

a) (6-Chloro-3-trifluoromethyl-pyridin-2-yl)-acetic acid tert-butyl ester and (6-chloro-5-trifluoromethyl-pyridin-2-yl)-acetic acid tert-butyl ester 1,1,1,3,3,3-Hexamethyldisilazane (33.4 ml, 154 mmol) is dissolved in toluene (180 ml). The solution is degassed by three cycles of briefly applying high vacuum and then purging with argon. After cooling the solution to −78° C., n-BuLi (96 ml of a 1.6 M solution in hexane, 154 mmol) is added dropwise during 20 minutes. The suspension is stirred for 15 minutes at −78° C. and for 15 minutes at RT, after which a clear yellow solution is obtained. Palladium(0) dibenzylidenacetone complex (1.69 g, 1.85 mmol) and (2'-dicyclohexylphosphanyl-biphenyl-2-yl)-dimethyl-amine (1.53 g, 3.88 mmol) are placed under argon atmosphere in a second flask. At RT, the toluene solution of the lithium hexamethyldisilazide is cannulated into the flask containing the palladium(0) complex—ligand mixture and stirred at RT for 10 minutes. After cooling to −10° C., acetic acid tert-butyl ester (19.0 ml, 142 mmol) is added dropwise during 5 minutes. After stirring for 10 minutes at −10° C., 2,6-dichloro-3-trifluoromethyl-pyridine (13.3 g, 61.58 mmol) is added in one portion. By applying gentle heating, the reaction mixture is warmed to 20° C. within 3 minutes after addition of the educt. The reaction temperature raises then gradually to approximately 50° C. After 15 minutes, TLC analysis indicates complete consumption of the starting 2,6-dichloro-3-trifluoromethyl-pyridine. The reaction is quenched by addition of water (100 ml) and stirring for 10 minutes. EtOAc (250 ml) is added, and the cloudy suspension is filtered through a pad of Celite. The organic layer is washed twice with water (backextracted), dried over Na$_2$SO$_4$ and concentrated. Purification by FCC (toluene/EtOAc 100:0, 99:1, 98:2, 97:3, 96:4 and 8:2) yields 10.15 g (56%) of a 1:2.5 mixture of regioisomeric (6-Chloro-3-trifluoromethyl-pyridin-2-yl)-acetic acid tert-butyl ester and (6-Chloro-5-trifluoromethyl-pyridin-2-yl)-acetic acid tert-butyl ester. Analytical data for (6-Chloro-3-trifluoromethyl-pyridin-2-yl)-acetic acid tert-butyl ester: $^1$H NMR (CDCl$_3$, 400 MHz) δ 1.56 (s, 9H), 3.89 (s, 2H), 7.47 (d, J=8.9 Hz, 1H), 8.04 (d, J=8.9 Hz, 1H); ES-MS: 296.3 [M+H]$^+$.

b) (6-Chloro-3-trifluoromethyl-pyridin-2-yl)-acetic acid ethyl ester

A 1:2.5 mixture of (6-chloro-3-trifluoromethyl-pyridin-2-yl)-acetic acid tert-butyl ester and (6-chloro-5-trifluoromethyl-pyridin-2-yl)-acetic acid tert-butyl ester (semi-crude; 10.15 g, 34.33 mmol) is dissolved in EtOH (100 ml) previously saturated at 0° C. with HCl gas. The solution is heated to 90° C. After 30 minutes at 90° C., TLC analysis indicates full conversion of the starting material. The solvent is completely evaporated. The crude reaction product is dissolved in EtOAc, washed once with conc. aqueous NaHCO$_3$ and once with H$_2$O (backextracted with EtOAc). The organic layer is dried over Na$_2$SO$_4$ and concentrated. Careful purification by FCC (hexanes/EtOAc 100:0, 97:3, 95:5, 9:1, 85:15, 8:2 to 7:3) separates the two regioisomeric compounds, (6-chloro-3-trifluoromethyl-pyridin-2-yl)-acetic acid tert-butyl ester and (6-chloro-5-trifluoromethyl-pyridin-2-yl)-acetic acid ethyl ester. Analytical data for (6-Chloro-3-trifluoromethyl-pyridin-2-yl)-acetic acid ethyl ester: $^1$H NMR (CDCl$_3$, 400 MHz) δ 1.28 (t, J=6.7 Hz, 3H), 3.95 (s, 2H), 4.12 (q, J=6.7 Hz, 2H), 7.32 (d, J=8.9 Hz, 1H), 7.85 (d, J=8.9 Hz, 1H); ES-MS: 268.2 [M+H]$^+$.

c) [6-(4-Methyl-piperazin-1-yl)-3-trifluoromethyl-pyridin-2-yl]-acetic acid ethyl ester (6-Chloro-3-trifluoromethyl-pyridin-2-yl)-acetic acid ethyl ester (700 mg, 2.62 mmol), palladium(II) acetate (47 mg, 0.21 mmol) and rac-2,2'-Bis-diphenylphosphanyl-[1,1'] binaphthalene (65 mg, 0.10 mmol) are added to sodium tert-butoxide, which has been dried for 15 minutes at 60° C. under high vacuum (277 mg, 2.88 mmol). This mixture is suspended in dioxane (9 ml, degassed three times under high vacuum and purged with argon), and N-methyl piperazine (288 mg, 2.88 mmol) is added. The flask containing this suspension is immersed in a pre-heated oil bath (85° C.). After 15 minutes at 85° C., TLC analysis indicates complete consumption of starting materials. The reaction mixture is cooled to RT and poured under stirring into a mixture of conc. aqueous NH$_4$Cl (100 ml) and EtOAc (100 ml). The aqueous layer is extracted with EtOAc. The organic layer is then washed once with conc. aqueous NH$_4$Cl, dried over Na$_2$SO$_4$ and concentrated. Purification by FCC (CH$_2$Cl$_2$/MeOH 100:0 to 98:2 to 97:3 to 96:4 to 95:5 to 8:2) yields the title compound. $^1$H NMR (CDCl$_3$, 400 MHz) δ 1.30 (t, J=7.8 Hz, 3H), 2.35 (s, 3H), 2.50-2.57 (m, 4H), 3.32-3.39 (m, 4H), 3.76 (s, 2H), 4.20 (q, J=7.8 Hz, 2H), 6.90 (d, J=8.9 Hz, 1H), 7.79 (d, J=8.9 Hz, 1H); ES-MS: 332.5 [M+H]$^+$.

d) [6-(4-Methyl-piperazin-1-yl)-3-trifluoromethyl-pyridin-2-yl]-acetic acid ethyl ester (493 mg, 1.49 mmol) and formamide (224 mg, 4.98 mmol) are dissolved under an atmosphere of argon in DMF (2.5 ml). The solution is heated to 105° C., and NaOMe (0.28 ml of a 5.4 M solution in MeOH, 1.49 mmol) is added dropwise during 30 minutes. After additional 10 minutes at 105° C., TLC analysis indicates complete consumption of starting materials. The reaction mixture is cooled to RT, diluted with water and extracted with CH$_2$Cl$_2$. The organic layers are dried over Na$_2$SO$_4$. Removal of solvent and drying under high vacuum affords a crude product, which is purified by FCC (EtOAc/AcOH/H$_2$O 700:110.90 to 650:130:120 to 600:150:150 to 500:200:200) to yield the title compound as its acetate salt. $^1$H NMR (DMSO, 400 MHz) δ 2.20 (s, 3H), 2.34-2.38 (m, 4H), 3.55 (s, 2H), 3.55-3.58 (m, 4H), 6.78 (d, J=10.6 Hz, 1H), 6.92 (br s, 1H), 7.32 (br s, 1H), 7.71 (d, J=10.6 Hz, 1H); ES-MS: 303.5 [M+H]$^+$.

By following the procedure of Example 1, but using the appropriate starting materials, the compounds of formula A wherein R$_a$, R$_b$, R$_2$ and R$_5$ to R$_7$ are as indicated in Table 1 below, may be obtained.

TABLE 1

A

| Example | $R_a$ | $R_b$ | $R_2$ | $R_5$ | $R_8$ | $R_7$ | M.S. Data |
|---|---|---|---|---|---|---|---|
| 2 | H | $CH_3$ | $CF_3$ | $CH_3$ | H | H | $MH^+$ 470 |
| 3 | H | Cl | $CF_3$ | $CH_3$ | H | H | $MH^+$ 490 |
| 4 | H | H | $CF_3$ | H | $-CH_2-CH_2-$ | | $MH^+$ 468 |
| 5 | H | $CH_3$ | $CF_3$ | H | $-CH_2-CH_2-$ | | $MH^+$ 482 |
| 6 | H | $CH_2-CH_3$ | $CF_3$ | H | $-CH_2-CH_2-$ | | $MH^+$ 496 |
| 7 | H | $CH_3$ | F | $CH_3$ | H | H | $MH^+$ 420 |
| 8 | H | H | F | $CH_3$ | H | H | $MH^+$ 406 |
| 9 | H | $CH_2-CH_3$ | F | $CH_3$ | H | H | $MH^+$ 434 |
| 10 | H | H | Cl | $CH_3$ | H | H | $MH^+$ 422 |
| 11 | H | $CH_2-CH_3$ | Cl | $CH_3$ | H | H | $MH^+$ 450 |
| 12 | H | $CH_3$ | Cl | $CH_3$ | H | H | $MH^+$ 436 |
| 13 | $CH_3$ | H | F | $CH_3$ | H | H | $MH^+$ 420 |
| 14 | H | Cl | F | $CH_3$ | H | H | $MH^+$ 440 |
| 15 | H | $CH_3$ | H | $CH_3$ | H | H | $MH^+$ 402 |
| 16 | H | H | H | $CH_3$ | H | H | $MH^+$ 388 |
| 17 | H | $CH_3$ | $CH_3$ | $CH_3$ | H | H | $MH^+$ 416 |
| 18 | H | H | $CH_3$ | $CH_3$ | H | H | $MH^+$ 402 |
| 19 | $CH_3$ | H | $CH_3$ | $CH_3$ | H | H | $MH^+$ 416 |
| 20 | H | $CH_3$ | $NO_2$ | $CH_3$ | H | H | $MH^+$ 447 |
| 21 | $CH_3$ | H | $NO_2$ | $CH_3$ | H | H | $MH^+$ 447 |
| 22 | H | H | $NO_2$ | $CH_3$ | H | H | $MH^+$ 433 |
| 23 | $CH_3$ | H | $NH_2$ | $CH_3$ | H | H | $MH^+$ 417 |
| 24 | H | $CH_3$ | $NH_2$ | $CH_3$ | H | H | $MH^+$ 417 |
| 25 | H | H | $NH_2$ | $CH_3$ | H | H | $MH^+$ 403 |
| 26 | H | H | CN | $CH_3$ | H | H | $MH^+$ 413 |
| 27 | H | $CH_3$ | CN | $CH_3$ | H | H | $MH^+$ 427 |
| 28 | $CH_3$ | H | CN | $CH_3$ | H | H | $MH^+$ 427 |

EXAMPLE 29

3-(5-Chloro-2-dimethylaminomethyl-1H-indol-4-yl)-4-(1H-indol-3-yl)-pyrrole-2,5-dione

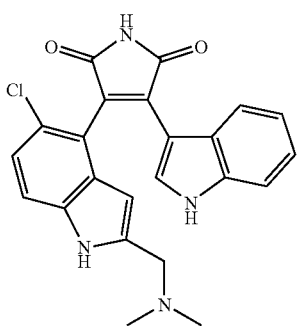

2-(5-Chloro-2-dimethylaminomethyl-1H-indol-4-yl)-acetamide (50 mg, 0.19 mmol) and (1H-indol-3-yl)-oxo-acetic acid methyl ester (57 mg, 0.28 mmol) are dissolved under an atmosphere of argon in 3 ml of dry THF. Molecular sieves (3 Å, 100 mg) are added. A solution of 1.0 M KOtBu in THF (0.57 ml) is added dropwise at RT over a period of 1 minute. After 1 hour, TLC analysis indicates complete consumption of starting materials. The reaction mixture was diluted with EtOAc and washed twice with saturated aq. NH4Cl and once with saturated aq. NaCl. The aqueous layers are backextracted with EtOAc. The combined organic layers are dried over $Na_2SO_4$ and the solvent evaporated to give a quantitative yield of crude 4-(5-chloro-2-dimethylaminomethyl-1H-indolyl)-3-hydroxy-3-(1H-indol-3-yl)-pyrrolidine-2,5-dione. This product is dissolved in dry DMF (4 ml) under an atmosphere of argon, and DBU (141 microL, 0.94 mmol) is added at RT. The reaction flask is then immersed in a oil-bath preheated to 120° C. for 10 minutes. TLC analysis indicates complete conversion of the starting material. The reaction mixture is diluted with EtOAc and washed with saturated aq. NaCl. The organic layer is dried over $Na_2SO_4$ and the solvent is evaporated. The residue is purified by FCC (EtOAc/AcOH/$H_2O$ 700:110:90 to afford the title compound as its acetate salt. $^1$H NMR (DMSO, 400 MHz) δ 1.96 (s, 6H), 3.30-3.42 (m, 2H), 5.86 (s, 1H), 6.38 (d, J=8.4 Hz, 1H), 6.51 (t, J=8.4 Hz, 1H), 6.94 (t, J=8.4 Hz, 1H), 7.29 (d, J=9.0 Hz, 1H), 7.32 (d, 8.4 Hz, 1H), 7.39 (d, J=9.0 Hz, 1H), 7.98 (s, 1H), 11.3 (s, 1H), 12.0 (br s, 2H); ES-MS: 419.1 $[M+H]^+$.

2-(5-Chloro-2-dimethylaminomethyl-1H-indolyl)-acetamide used as starting material may be prepared as follows:

a) 5-Chloro-2-methyl-4-nitro-1H-indole

4-Chloro-3-nitroaniline (10.0 g, 57.9 mmol) is dissolved in DMSO (130 ml). Acetone (8.52 ml, 115.9 mmol) and potassium tert-butylate (13.0 g, 115.9 mmol) are added. The temperature is kept below 30° C. by the use of an ice bath. After 90 minutes at RT, TLC analysis indicated complete conversion of the starting material. The reaction mixture is poured on water, acidified with aqueous 2M HCl, and then extracted with EtOAc. The organic layer is washed with saturated aqueous NaCl solution, dried over $Na_2SO_4$ and concentrated. Purification by FCC ($CH_2Cl_2$) affords a slightly brownish solid, which by $^1$H-NMR analysis is an approximately 1:1 mixture of the desired title compound and the corresponding de-chlorinated derivative. Careful purification by preparative HPLC affords the title compound. $^1$H NMR (DMSO, 400 MHz) δ 2.50 (s, 3H), 6.40 (s, 1H), 7.26 (d, J=9.0 Hz, 1H), 7.61 (d, J=9.0 Hz, 1H), 11.8 (s, 1H); ES-MS: 209 $[M-H]^-$.

b) 5-Chloro-2-methyl-4-nitro-indole-1-carboxylic acid methyl ester

5-Chloro-2-methyl-4-nitro-1H-indole (1.62 g, 7.69 mmol) is dissolved under an atmosphere of argon in dry DMF (30 ml). After addition of a NaH suspension (60% in mineral oil, 369 mg, 9.22 mmol) the mixture is stirred for 1 hour at RT. Methyl chloroformate (0.72 ml, 9.22 mmol) is added slowly during 10 minutes, and the reaction mixture is stirred at RT for 1 hour to form a yellowish suspension. After filtration and drying, the title compound is obtained in pure form. $^1$H NMR (DMSO, 400 MHz) δ 2.53 (s, 3H), 4.06 (s, 3H), 6.71 (s, 1H), 7.57 (d, J=9.0 Hz, 1H), 8.30 (d, J=9.0 Hz, 1H); ES-MS: 268 $[M+H]^+$.

c) 4-Amino-5-chloro-2-methyl-indole-1-carboxylic acid methyl ester

5-Chloro-2-methyl-4-nitro-indole-1-carboxylic acid methyl ester (2.1 g, 7.81 mmol) is dissolved in ethanol (40 ml) and glacial acetic acid (40 ml). Iron powder (1.74 g, 31.26 mmol, activated previously with $H_2SO_4$ conc and then washed with water) is added, and the reaction mixture is heated to 85° C. for 90 minutes. The reaction mixture is poured into water and stirred at RT for 30 minutes, after which a slightly brownish colored precipitate forms which is filtered off. After washing with water and drying, the title compound is obtained in pure form. $^1$H NMR (DMSO, 400 MHz, 120° C.) δ 2.51 (s, 3H), 4.05 (s, 3H), 5.0-5.2 (br s, 2H), 6.66 (s, 1H), 7.05 (d, J=9 Hz, 1H), 7.31 (d, J=9 Hz, 1H); ES-MS: 238 [M+H]$^+$.

d) 4-Bromo-5-chloro-2-methyl-indole-1-carboxylic acid methyl ester

4-Amino-5-chloro-2-methyl-indole-1-carboxylic acid methyl ester (2.04 g, 8.54 mmol) is suspended in a 4.8% solution of HBr in water (75 ml). After cooling to 0° C., a solution of sodium nitrite (1.23 g, 17.94 mmol) in water (30 ml) is slowly added during 20 minutes. After 30 minutes at 0° C., it is slowly added to a solution of copper(I) bromide (25.1 g, 175 mmol) in 48% HBr/H$_2$O (75 ml), while the temperature is kept below 5° C. After the addition is complete, the suspension is stirred at RT for 2 hours and then at 85° C. for 5 minutes. After cooling to RT, the mixture is extracted with CH$_2$Cl$_2$/MeOH (95:5, 800 ml). The organic layer is washed with saturated aqueous NaCl solution, dried over Na$_2$SO$_4$ and concentrated. Purification by FCC (hexane/EtOAc 4:1) affords the title compound. $^1$H NMR (DMSO, 400 MHz) δ 2.61 (s, 3H), 4.03 (s, 3H), 6.56 (s, 3H), 7.46 (d, J=9 Hz, 1H), 8.05 (d, J=9 Hz, 1H); ES-MS: 303 [M+H]$^+$.

e) 5-Chloro-4-ethoxycarbonylmethyl-2-methyl-indole-1-carboxylic acid methyl ester 4-Bromo-5-chloro-2-methyl-indole-1-carboxylic acid methyl ester (1.99 g, 6.57 mmol) and tributylstannanyl-acetic acid ethyl ester (3.22 g, 8.55 mmol) are dissolved in dry DMF (55 ml) under an atmosphere of argon. Zinc(II) bromide (1.92 g, 8.55 mmol) and dichlorobis(tri-o-tolylphosphin)palladium (0) (1.03 g, 1.31 mmol) are added. The reaction mixture is heated to 80° C. for 18 hours. TLC analysis indicates complete consumption of the starting material. The reaction mixture is cooled to RT and poured on a saturated aqueous solution of NH$_4$Cl. After addition of EtOAc (30 ml), the mixture is filtered through a pad of Celite. The organic layer is washed with saturated aq. NaCl solution, dried over Na$_2$SO$_4$ and concentrated. The residue is purified by FCC (hexane/EtOAc 4:1) to yield the desired compound, still contaminated with tin residues. The mixture is dissolved in a 1:1 mixture of 1 M NaOH/EtOAc (200 ml in total) and stirred at RT for 18 hours. The organic layer is separated, washed once with concentrated aqueous NaCl solution, and then dried over Na$_2$SO$_4$. Concentration yields a solid residue which is purified by FCC (hexane/EtOac 4:1) to afford the desired compound, still slightly contaminated. A further round of purification with an automated preparative HPLC system (Gilson HPLC, Xterra 5 mikron, gradient 10% to 100% MeCN in H$_2$O, 30 min) affords the pure title compound. $^1$H NMR (DMSO, 400 MHz) δ 1.20 (t, J=6.6 Hz, 3H), 2.59 (s, 3H), 4.01 (s, 2H), 4.03 (s, 3H), 4.11 (q, J=6.6 Hz, 2H), 6.68 (s, 1H), 7.32 (d, J=9 Hz, 1H), 7.96 (d, J=9 Hz, 1H); ES-MS: 332.1 [M+Na]$^+$.

f) 5-Chloro-4-ethoxycarbonylmethyl-2-formyl-indole-1-carboxylic acid methyl ester 5-Chloro-4-ethoxycarbonylmethyl-2-methyl-indole-1-carboxylic acid methyl ester (398 mg, 1.28 mmol) is dissolved under an atmosphere of argon in dioxane (18 ml). Selenious acid (331 mg, 2.56 mmol) is added, and the reaction mixture is heated to 100° C. for 18 hours. TLC analysis indicates complete conversion of the starting material. The reaction mixture is diluted with EtOAc and poured on water. The organic layer is washed with saturated aqueous NaCl solution, dried over Na$_2$SO$_4$ and concentrated. The solid residue is purified by FCC (hexane/EtOAc 2:1) to afford the title compound. $^1$H NMR (DMSO, 400 MHz) δ 1.20 (t, J=6.6 Hz, 3H), 4.09 (s, 3H), 4.12 (q, J=6.6 Hz, 2H), 4.19 (s, 2H), 7.64 (d, J=10.8, 1H), 8.09 (d, J=10.8, 1H), 10.32 (s, 1H); ES-MS: 346.1.1 [M+Na]$^+$.

g) (5-Chloro-2-dimethylaminomethyl-1H-indol-4-yl)-acetic acid ethyl ester

5-Chloro-4-ethoxycarbonylmethyl-2-formyl-indole-1-carboxylic acid methyl ester (350 mg, 1.08 mmol) is dissolved in dry THF (10 ml) under an atmosphere of argon, and dimethylamine (290 microL of a 5.6 M solution in EtOH, 1.62 mmol) is added at RT. The reaction mixture is stirred at RT for 18 hours. A solution of sodium cyanoborohydride (82 mg, 1.29 mmol) in methanol (3 ml) and acetic acid (310 microL, 5.40 mmol) is then added. Stirring is continued for 3 hours at RT. TLC analysis indicates complete conversion of the starting material. The reaction mixture is diluted with EtOAc and poured on water. The pH is made alkaline by the addition of a saturated aqueous solution of NaHCO$_3$. The aqueous layer is extracted with EtOAc, and the combined organic layers are washed once with concentrated aqueous NaCl solution. After drying over Na$_2$SO$_4$, the solvent is removed and the residue is purified by FCC (CH$_2$Cl$_2$/EtOH/aq. NH$_3$ 90:9:1) to give the title compound. $^1$H NMR (DMSO, 400 MHz) δ 1.19 (t, J=6.6 Hz, 3H), 2.20 (s, 6H), 3.55 (s, 2H), 3.97 (s, 2H), 4.11 (q, J=6.6 Hz, 2H), 6.38 (s, 1H), 7.08 (d, J=9.0 Hz, 1H), 7.26 (d, J=9.0 Hz, 1H), 11.2 (br s, 1H); ES-MS: 293.2 [M+H]$^-$.

h) (5-Chloro-2-dimethylaminomethyl-1H-indol-4-yl)-acetic acid ethyl ester (187 mg, 0.63 mmol) and formamide (84 microL, 2.12 mmol) are dissolved under an atmosphere of argon in dry DMF (1.5 ml). The solution is heated to 105° C., and NaOMe (118 microL of a 5.4 M solution in MeOH, 0.63 mmol) is added dropwise during 10 minutes. After 1 hour at 105° C., TLC analysis indicates complete consumption of the starting material. The reaction mixture is cooled to RT, diluted with water, and the pH value is adjusted to 7 by addition of aqueous 1 M NaHSO$_4$. The mixture is concentrated, and the solid residue is purified by FCC (CH$_2$Cl$_2$/EtOH/aq NH$_3$ 70:27:3) to afford the title compound. ES-MS: 266.7 [M+H]$^+$.

By following the procedure of Example 29 but using the appropriate starting materials, the compounds of formula B, wherein R$_a$, R$_b$ and R$_4$ are as indicated in Table 2, may be prepared.

TABLE 2

B

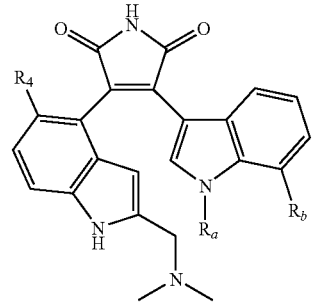

| Example | R$_a$ | R$_b$ | R$_4$ | M.S. Data |
|---|---|---|---|---|
| 30 | CH$_3$ | CH$_3$ | Cl | MH$^+$ 447 |
| 31 | i-Pr | H | Cl | MH$^+$ 461 |
| 32 | CH$_3$ | H | Cl | MH$^+$ 433 |
| 33 | CH$_3$ | CH$_3$ | CH$_3$ | MH$^+$ 427 |
| 34 | H | CH$_3$ | CH$_3$ | MH$^+$ 413 |

TABLE 2-continued

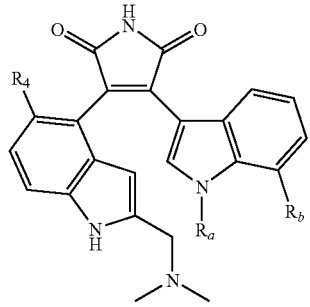

B

| Example | $R_a$ | $R_b$ | $R_4$ | M.S. Data |
|---|---|---|---|---|
| 35 | H | H | $CH_3$ | $MH^+$ 399 |
| 36 | $CH_3$ | H | $CH_3$ | $MH^+$ 413 |
| 37 | $CH_3$ | $CH_3$ | H | $MH^+$ 413 |
| 38 | H | $CH_3$ | H | $MH^+$ 399 |
| 39 | $CH_3$ | H | H | $MH^+$ 399 |
| 40 | H | H | H | $MH^+$ 385 |
| 41 | H | H | Cl | $MH^+$ 434 |
| 42 | H | $CH_3$ | F | $MH^+$ 417 |
| 43 | H | H | F | $MH^+$ 403 |
| 44 | $CH_3$ | H | F | $MH^+$ 417 |

By following the procedure of Example 29 but using the appropriate starting materials, the compounds of formula C, wherein $R_a$, $R_b$, $R_4$, $R_8$ and $R_9$ are as indicated in Table 3, may be prepared.

TABLE 3

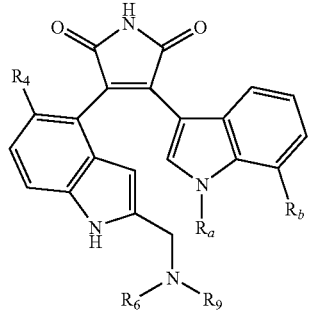

C

| Example | $R_a$ | $R_b$ | $R_4$ | $R_8$ | $R_9$ | M.S. Data |
|---|---|---|---|---|---|---|
| 45 | H | H | Cl | H | —$CH_2$-cyclopropyl | $MH^+$ 446 |
| 46 | H | $CH_3$ | Cl | H | —$CH_2$-cyclopropyl | $MH^+$ 460 |
| 47 | H | H | Cl | $CH_3$ | —$CH_2$-cyclopropyl | $MH^+$ 460 |
| 48 | H | $CH_3$ | Cl | $CH_3$ | —$CH_2$-cyclopropyl | $MH^+$ 474 |
| 49 | $CH_3$ | H | H | $CH_3$ | —$CH_2$-cyclopropyl | $MH^+$ 426 |
| 50 | H | H | H | $CH_3$ | —$CH_2$-cyclopropyl | $MH^+$ 411 |
| 51 | $CH_3$ | H | H | H | —$CH_2$-cyclopropyl | $MH^+$ 411 |
| 52 | H | H | Cl | H | —$CH_2$—$CH_2$F | $MH^+$ 438 |
| 53 | H | $CH_3$ | Cl | H | —$CH_2$—$CH_2$F | $MH^+$ 452 |
| 54 | H | H | Cl | H | —$CH_2$—$CH_2$—$OCH_3$ | $MH^+$ 450 |
| 55 | H | $CH_3$ | Cl | H | —$CH_2$—$CH_2$—$OCH_3$ | $MH^+$ 464 |
| 56 | H | H | Cl | $CH_3$ | —$CH_2$—$CH_2$—$OCH_3$ | $MH^+$ 464 |
| 57 | H | $CH_3$ | Cl | $CH_3$ | —$CH_2$—$CH_2$—$OCH_3$ | $MH^+$ 478 |
| 58 | H | H | Cl | H | —$CH_2$—CH=$CH_2$ | $MH^+$ 432 |
| 59 | H | $CH_3$ | Cl | H | —$CH_2$—CH=$CH_2$ | $MH^+$ 446 |
| 60 | H | H | Cl | $CH_3$ | —$CH_2$—CH=$CH_2$ | $MH^+$ 460 |
| 61 | H | $CH_3$ | Cl | $CH_3$ | —$CH_2$—CH=$CH_2$ | $MH^+$ 474 |
| 62 | H | H | Cl | H | —$CH_2$—$CH_2$—$N(CH_3)_2$ | $MH^+$ 463 |
| 63 | H | $CH_3$ | Cl | H | —$CH_2$—$CH_2$—$N(CH_3)_2$ | $MH^+$ 477 |

TABLE 3-continued

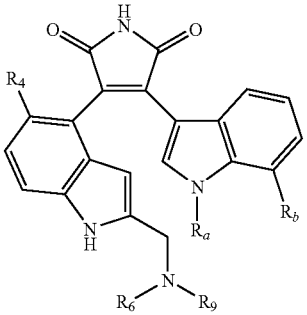

C

| Example | $R_a$ | $R_b$ | $R_4$ | $R_8$ | $R_9$ | M.S. Data |
|---|---|---|---|---|---|---|
| 64 | $CH_3$ | H | H | H | phenyl | $MH^+$ 462 |
| 65 | $CH_3$ | H | H | $CH_3$ | phenyl | $MH^+$ 476 |
| 66 | H | $CH_3$ | Cl | —$CH_2$—$CH_2$—N—$CH_2$—$CH_2$— | | $MH^+$ 489 |
| 67 | $CH_3$ | H | Cl | —$CH_2$—$CH_2$—N—$CH_2$—$CH_2$— | | $MH^+$ 489 |
| 68 | H | H | Cl | —$CH_2$—$CH_2$—N—$CH_2$—$CH_2$— | | $MH^+$ 475 |

The compounds of formula I in free form or in pharmaceutically acceptable salt form exhibit valuable pharmacological properties, e.g. inhibiting Protein Kinase C (PKC), e.g. PKC isoforms like α, β, δ, ε, η or θ activity, inhibiting T-cell activation and proliferation, e.g. by inhibiting production by T-cells or cytokines, e.g. IL-2, by inhibiting the proliferative response of T-cells to cytokines, e.g. IL-2, e.g. as indicated in in vitro and in vivo tests and are therefore indicated for therapy.

A. In Vitro

1. Protein Kinase C Assay

The compounds of formula I are tested for their activity on different PKC isoforms according to a published method (D. Geiges et al. Biochem. Pharmacol. 1997; 53:865-875) The assay is performed in a 96-well polypropylene microtiterplate (Costar 3794) that has been previously siliconized with Sigmacote (Sigma SL-2). The reaction mixture (50 μl) contains 10 μl of the relevant PKC isozyme together with 25 μl of the test compound and 15 μl of a mix solution that contains 200 μg/ml protamine sulfate, 10 mM $Mg(NO_3)_2$, 10 μM ATP (Boehringer 519987) and 3750 Bq of $^{33}$P-ATP (Hartmann Analytic SFC301, 110 TBq/mmol) in 20 mM Tris-buffer pH 7.4+0.1% BSA. Incubation is performed for 15 min at 32° C. in a microtiterplate shaking incubator (Biolabo Scientific Instruments). Reaction is stopped by adding 10 μl of 0.5 M $Na_2EDTA$, pH 7.4. 50 μl of mixture are pipetted onto a pre-wetted phosphocellulose paper (Whatmann 3698-915) under gentle pressure. Non-incorporated ATP is washed away with 100 μl bi-dist $H_2O$. The paper is washed twice in 0.5% $H_3PO_4$ for 15 min followed by 5 min in EtOH. Thereafter the paper is dryed and placed in an omnifilter (Packard 6005219), and overlayed with 10 μl/well of Microscint-O (Packard 6013611) before counting in a Topcount radioactivity counter (Packard). $IC_{50}$ measurement is performed on a routine basis by incubating a serial dilution of inhibitor at concentrations ranging between 1-1000 μM according to the method described above. $IC_{50}$ value are calculated from the graph by sigmoidal curve fitting.

2. Protein Kinase C θ Assay

Human recombinant PKCθ is used under the assay conditions as described above. In this assay, compounds of formula I inhibit PKC θ with an $IC_{50} \leq 1$ μM. For example, compound of Example 1 inhibits PKCθ with an $IC_{50}$ of 5.4 nM, compound of Example 10 with an $IC_{50}$ of 5.8 nM and compound of Example 41 inhibits PKCθ with an $IC_{50}$ of 9.3 nM.

3. Protein Kinase Cα Assay

Human recombinant PKCα was obtained from Oxford Biomedical Research and is used under the assay conditions as described under Section A.1 above. In this assay, compounds of formula I inhibit PKCα with an $IC_{50} \leq 1$ μM. In this assay, compound of Example 1 inhibits PKCα with an $IC_{50}$ of 2.9 nM, compound of Example 39 inhibits PKCα with an $IC_{50}$ of 6.3 nM and compound of Example 41 inhibits PKCα with an $IC_{50}$ of 7.5 nM.

4. Protein Kinase Cβ1 Assay

Human recombinant PKCβ1 was obtained from Oxford Biomedical Research and is used under the assay conditions as described under Section A.1 above. In this assay, compounds of formula I inhibit PKCβ1 with an $IC_{50} \leq 1$ μM. For example, compound of Example 1 inhibits PKCβ1 with an $IC_{50}$ of 5.9 nM, compound of Example 39 inhibits PKCβ1 with an $IC_{50}$ of 13.2 nM and compound of Example 41 inhibits PKCβ1 with an $IC_{50}$ of 14.9 nM.

5. Protein Kinase Cδ Assay

Human recombinant PKCδ was obtained from Oxford Biomedical Research and is used under the assay conditions as described under Section A.1 above. In this assay, compounds of formula I inhibit PKCδ with an $IC_{50} \leq 1$ μM. For example, compound of Example 1 inhibits PKCδ with an $IC_{50}$ of 21.0 nM and compound of Example 41 inhibits PKCδ with an $IC_{50}$ of 29.5 nM.

6. Protein Kinase Cε Assay

Human recombinant PKCε was obtained from Oxford Biomedical Research and is used under the assay conditions as described under Section A.1 above. In this assay, compounds of formula I inhibit PKCε with an $IC_{50} \leq 1$ μM. For example, compound of Example 1 inhibits PKCδ with an $IC_{50}$ of 14.7 nM and compound of Example 41 inhibits PKCδ with an $IC_{50}$ of 7.6 nM.

7. Protein Kinase Cη Assay

Human recombinant PKCη was obtained from PanVera and is used under the assay conditions as described under Section A.1 above. In this assay, compounds of formula I inhibit PKCη with an $IC_{50} \leq 1$ μM. For example, compound of Example 1 inhibits PKCη with an $IC_{50}$ of 15.3 nM and compound of Example 41 inhibits PKCη with an $IC_{50}$ of 15.0 nM 8. CD28 Costimulation Assay The assay is performed with Jurkat cells transfected with a human interleukin-2 promoter/reporter gene construct as described by Baumann G et al. in Transplant Proc. 1992; 24:43-8, the β-galactosidase reporter gene being replaced by the luciferase gene (de Wet J., et al., Mol. Cell Biol. 1987, 7(2), 725-737). Cells are stimulated by solid phase-coupled antibodies or phorbol myristate acetate (PMA) and the $Ca^{++}$ ionophore ionomycin as follows. For antibody-mediated stimulation Microlite TM1 microtiter plates (Dynatech) are coated with 3 μg/ml goat anti-mouse IgG Fc antibodies (Jackson) in 55 μl phosphate-buffered saline (PBS) per well for three hours at RT. Plates are blocked after removing the antibodies by incubation with 2% bovine serum albumin (BSA) in PBS (300 μl per well) for 2 hours at RT. After washing three times with 300 μl PBS per well, 10 ng/ml anti-T cell receptor antibodies (WT31, Becton & Dickinson) and 300 ng/ml anti-CD28 antibodies (15E8) in 50 μl 2% BSA/PBS are added as stimulating antibodies and incubated overnight at 4° C. Finally the plates are washed three times with 300 μl PBS per well. Seven three-fold serial dilutions of test compounds in duplicates in assay medium (RPMI 1640/10% fetal calf serum (FCS) containing 50 μM 2-mercaptoethanol, 100 units/ml penicillin and 100 μg/ml streptomycin) are prepared in separate plates, mixed with transfected Jurkat cells (clone K22 290_H23) and incubated for 30 minutes at 37° C. in 5% $CO_2$. 100 μl of this mixture containing $1 \times 10^5$ cells are then transferred to the antibody-coated assay plates. In parallel 100 μl are incubated with 40 ng/ml PMA and 2 μM ionomycin. After incubation for 5.5 hours at 37° C. in 5% $CO_2$, the level of luciferase is determined by bioluminescence measurement. The plates are centrifuged for 10 min at 500 g and the supernatant is removed by flicking. Lysis buffer containing 25 mM Tris-phosphate, pH 7.8, 2 mM DTT, 2 mM 1.2-diaminocyclohexane-N,N,N',N-tetraacetic acid, 10% (v/v) glycerol and 1% (v/v) Triton X-100 is added (20 μl per well). The plates are incubated at RT for 10 minutes under constant shaking. Luciferase activity is assessed with a bioluminescence reader (Labsystem, Helsinki, Finland) after automatic addition of 50 μl per well luciferase reaction buffer containing 20 mM Tricine, 1.07 mM $(MgCO_3)_4Mg(OH)_2 \times 5H_2O$, 2.67 mM $MgSO_4$, 0.1 mM EDTA, 33.3 mM DTT, 270 μM coenzyme A, 470 μM luciferin (Chemie Brunschwig AG), 530 μM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition ($IC_{50}$) is determined from the dose-response curves. In this assay, compounds of formula I inhibit anti-T cell receptor/anti-CD28 and PMA/ionomycin stimulated Jurkat cells with an $IC_{50} \leq 1$ μM.

For example, compound of Example 1 has an $IC_{50}$ of 13.0 nM, compound of Example 39 has an $IC_{50}$ of 46.7 nM and compound of Example 41 has an $IC_{50}$ of 28.3 nM.

9. Allogeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% FCS, 100 U/ml penicillin, 100 μg/ml streptomycin (Gibco BRL, Basel, Switzerland), 50 μM 2-mercaptoethanol (Fluka, Buchs, Switzerland) and serially diluted compounds. Seven three-fold dilution steps in duplicates per test compound are performed. After four days of incubation 1 μCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined. For example, compound of Example 1 has an $IC_{50}$ of 28.8 nM, compound of Example 39 has an $IC_{50}$ of 285 nM and compound of Example 41 has an $IC_{50}$ of 32.5 nM.

10. Inhibition of GSK-3β

The GSK-3β bidding assay is performed in 50 μl reactions in 96 well polypropylene plate, each reaction containing 20 mM magnesium chloride, 40 μM ATP, 2 mM DTT, 88.5 μM biotinylated and phosphorylated CREB-peptide substrate (biotin-KRREILSRRPS(PO$_4$)YR—OH; Q. M. Wang et al., J. Biol. Chem. 269, 14566-14574, 1994), [γ-$^{33}$P]ATP (1 μCi) and 2 μl of the compound to be tested in DMSO (various concentrations). 15 μl of GSK-3β (various concentrations) is added and the mixture is incubated at 30° C. for 1 hour. The reaction is stopped by transferring 25 μl of the mixture to a phosphocellulose plate containing 130 μl of 1.85% phosphoric acid. The free radionucleotides in the membrane are washed off under vacuum with 1.85% phosphoric acid (5 times). After the last wash, the plate is transferred to an adaptor plate and 50 μl of scintillation cocktail (Microscint-20, Packard, cat. # 20-133) is added to each well and the amount of radioactivity is counted in a top counter. Compounds of formula I are active in this assay.

For example, compound of Example 1 has an IC$_{50}$ of 18 nM and compound of Example 41 has an IC$_{50}$ of 25 nM.

B. In Vivo

Rat Heart Transplantation

The strain combination used: Male Lewis (RT$^1$ haplotype) and BN (RT$^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 10/0 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when heart beat stops. Increases of graft survival are obtained in animals treated with a compound of formula I administered orally at a daily dose of 1 to 30 mg/kg bid.

Graft v. Host Model

Spleen cells (2×10$^7$) from Wistar/F rats are injected subcutaneously into the right hind footpad of (Wistar/F×Fischer 344)F$_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound. In this assay, an inhibition of 100% is obtained with compound of Example 1 or 10 when administered at a dose of 30 or 10 mg/kg bid, respectively.

The compounds of formula I are, therefore, useful in the treatment and/or prevention of diseases or disorders mediated by T lymphocytes and/or PKC, e.g. acute or chronic rejection of organ or tissue allo- or xenografts, graft versus host diseases, atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as AIDS, septic shock or adult respiratory distress syndrome, ischemia/reperfusion injury e.g. myocardial infarction, stroke, gut ischemia, renal failure or hemorrhage shock, or traumatic shock, e.g. traumatic brain injury. The compounds of formula I are also useful in the treatment and/or prevention of T-cell mediated acute or chronic inflammatory diseases or disorders or autoimmune diseases e.g. rheumatoid arthritis, osteoarthritis, systemic lupus erythematosus, Hashimoto's thyroidis, multiple sclerosis, myasthenia gravis, diabetes type I or II and the disorders associated therewith, respiratory diseases such as asthma or inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis. For the above uses the required dosage will of course vary depending on the mode of administration, the particular condition to be treated and the effect desired. In general, satisfactory results are indicated to be obtained systemically at daily dosages of from about 0.1 to about 100 mg/kg body weight An indicated daily dosage in the larger mammal, e.g. humans, is in the range from about 0.5 mg to about 2000 mg, conveniently administered, for example, in divided doses up to four times a day or in retard form.

The compounds of formula I may be administered by any conventional route, in particular enterally, e.g. orally, e.g. In the form of tablets or capsules, or parenterally, e.g. In the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

Topical administration is e.g. to the skin. A further form of topical administration is to the eye.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by T lymphocytes and/or PKC or GSK-3β, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g. in any of the methods as indicated under 1.1 and 1.2 above.

3. A pharmaceutical composition, e.g. for use in any of the methods as in 1.1 and 1.2 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 and 1.2 above.

Compounds of formula I may be administered as the sole active ingredient or together with other drugs in immunomodulating regimens or other anti-inflammatory agents e.g. for the treatment or prevention of allo- or xenograft acute or chronic rejection or inflammatory or autoimmune disorders. For example, they may be used in combination with cyclosporines, or ascomycines or their immunosuppressive analogs or derivatives, e.g. cyclosporin A, ISA Tx247, FK-506, ABT-281, ASM 981; an mTOR inhibitor, e.g. rapamycin, 40-O-(2-hydroxyethyl)-rapamycin, CCI779, ABT578, or a rapalog, e.g. AP23573, AP23464, AP23675, AP23841, TAFA-93, biolimus 7 or biolimus 9 etc.; corticosteroids; cyclophosphamide; azathioprene; methotrexate; an EDG receptor agonist having accelerating lymphocyte homing properties, e.g. FTY 720 or an analogue thereof; leflunomide or analogs thereof; mizoribine; mycophenolic acid; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA-4 antagonists. Compounds of formula I may also be administered together with an antiproliferative drug, e.g. a chemotherapeutic drug, e.g. as used in cancer treatment, including but not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide, or with an anti-diabetic drug, an insulin secretagogue or insulin secretion enhancer, e.g. a sulphonyl urea, e.g. tolbutamide, chlorpropamide, tolazamide, acetohexamide, 4-chloro-N-[(1-pyrolidinylamino)-carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide or tolylcyclamide, an oral insulinotropic agent derivative, e.g. a short acting insulin enhancer, e.g. meglitinide, repaglinide, a phenyl acetic acid derivative, e.g. nateglinide, a DPP IV inhibitor, e.g. 1-{2-[(5-cyanopyridin-2-yl)amino] ethylamino}acetyl-(2S)-cyano-pyrrolidine dihydrochloride, LAF237, GLP-1 or a GLP-1 agonist analog, or an insulin sensitizer e.g. a peroxisome proliferator activated receptor γ agonist (PPARγ), e.g. a glitazone, a non-glitazone type such as a N-(2-benzoylphenyl)-L-tyrosine analogue, e.g. GI-262570, or an oxolidinedione, e.g. JTT501, a dual PPARγ/PPARα agonist, e.g. DRF-554158, NC-2100 or NN-622, a retinoid X receptor agonist or a rexinoid, e.g. 2-[1-(3,5,5,8, 8-pentamethyl-5,6,7,8-tetrahydro-2-naphthyl)-cyclopropyl]-pyridine-5-carboxylic acid, 4-[(3,5,5,8,8-pentamethyl-5,6,7,8-tetrahydro-2-naphthyl)-2-carbonyl]-benzoic acid, 9-cis retinoic acid or an analog, derivative or a pharmaceutically acceptable salt thereof, in diabetes therapy.

In accordance with the foregoing the present invention provides in a yet further aspect:

5. A method as defined above comprising co-administration, e.g. concomitantly or in sequence, of a therapeutically effective amount of an inhibitor of GSK-3β, PKC or of T-cell activation and proliferation, e.g. a compound of formula I in free form or in pharmaceutically acceptable salt form, and a second drug substance, said second drug substance being an immunosuppressant, immunomodulatory, anti-inflammatory, antiproliferative or anti-diabetic drug, e.g. as indicated above.

6. A therapeutic combination, e.g. a kit, comprising a) an inhibitor of GSK-3β, PKC or of T-cell activation and proliferation, e.g. a compound of formula I in free form or in pharmaceutically acceptable salt form, and b) at least one second agent selected from an immunosuppressant, immunomodulatory, anti-inflammatory, antiproliferative and anti-diabetic drug. Component a) and component b) may be used concomitantly or in sequence. The kit may comprise instructions for its administration.

Where an inhibitor of GSK-3β, PKC or of T-cell activation and proliferation, e.g. a compound of formula I, is administered in conjunction with other immunosuppressive/immunomodulatory, anti-inflammatory, antiproliferative or anti-diabetic therapy, e.g. for preventing or treating acute or chronic graft rejection or inflammatory or autoimmune disorders as hereinabove specified, dosages of the co-administered immunosuppressant, immunomodulatory, anti-inflammatory, antiproliferative or anti-diabetic compound will of course vary depending on the type of co-drug employed, e.g. whether it is a steroid or a cyclosporine, on the specific drug employed, on the condition being treated and so forth.

The invention claimed is:

1. A compound selected from the compounds of formula A:

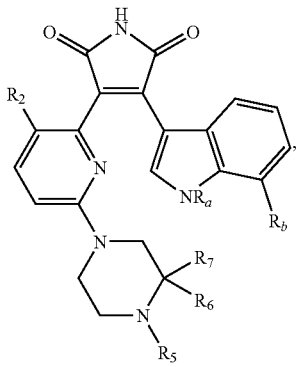

A wherein the substituents for each compound thereof have the following values:

| Compound | $R_a$ | $R_b$ | $R_2$ | $R_5$ | $R_6$ | $R_7$ |
|---|---|---|---|---|---|---|
| 1 | H | $CH_3$ | $CF_3$ | $CH_3$ | H | H |
| 2 | H | $CH_3$ | $CF_3$ | H | —$CH_2$—$CH_2$— | |
| 3 | H | $CH_3$ | F | $CH_3$ | H | H |
| 4 | H | H | F | $CH_3$ | H | H |
| 5 | H | H | Cl | $CH_3$ | H | H |
| 6 | H | $CH_3$ | Cl | $CH_3$ | H | H |
| 7 | H | $CH_3$ | $NO_2$ | $CH_3$ | H | H |
| 8 | H | H | $NO_2$ | $CH_3$ | H | H | or a salt thereof.

2. A compound according to claim 1, wherein $R_a$ is H, $R_b$ is H, $R_2$ is F, $R_5$ is $CH_3$, $R_6$ is H and $R_7$ is H; or $R_a$ is H, $R_b$ is H, $R_2$ is Cl, $R_5$ is $CH_3$, $R_6$ is H and $R_7$ is H.

3. A compound according to claim 1 that is 3-(1H-indol-3-yl)-4-[6-(4-methyl-piperazin-1-yl)-3-trifluoromethyl-pyridin-2-yl]-pyrrole-2,5-dione, or a pharmaceutically-acceptable salt thereof.

4. A pharmaceutical composition comprising a compound of formula A of claim 1, in free form or in a pharmaceutically-acceptable salt form, in association with a pharmaceutically-acceptable diluent or carrier therefor.

5. A pharmaceutical composition comprising a compound according to claim 3, in free form or in a pharmaceutically-acceptable salt form, in association with a pharmaceutically-acceptable diluent or carrier therefor.

6. A method for treating acute or chronic transplant rejection in a subject in need of such treatment, which method comprises administering to said subject an effective amount of a compound of formula A according to claim 1 or a pharmaceutically-acceptable salt thereof.

7. A method for treating acute or chronic transplant rejection in a subject in need of such treatment, which method comprises administering to said subject an effective amount of a compound according to claim 3.

8. A method for treating T-cell-mediated inflammatory or autoimmune diseases, wherein the T-cell-mediated inflammatory or autoimmune disease is selected from the group consisting of rheumatoid arthritis, osteoarthritis, systemic lupus erythematosus, Hashimoto's thyroidis, multiple sclerosis, myasthenia gravis, diabetes type I or II, asthma, inflammatory lung injury, inflammatory liver injury, inflammatory glomerular injury, psoriasis, atopic dermatitis, allergic contact dermatitis, irritant contact dermatitis, seborrhoeic dermatitis, Sjoegren's syndrome, keratoconjunctivitis, uveitis, inflammatory bowel disease, Crohn's disease, and ulcerative colitis, in a subject in need of such treatment, which method comprises administering to said subject a therapeutically-effective amount of a compound of formula A according to claim 1, or a pharmaceutically-acceptable salt thereof.

9. A method for treating T-cell-mediated inflammatory or autoimmune diseases, wherein the T-cell-mediated inflammatory or autoimmune disease is selected from the group consisting of rheumatoid arthritis, osteoarthritis, systemic lupus erythematosus, Hashimoto's thyroidis, multiple sclerosis, myasthenia gravis, diabetes type I or II, asthma, inflammatory lung injury, inflammatory liver injury, inflammatory glomerular injury, psoriasis, atopic dermatitis, allergic contact dermatitis, irritant contact dermatitis, seborrhoeic dermatitis, Sjoegren's syndrome, keratoconjunctivitis, uveitis, inflammatory bowel disease, Crohn's disease, and ulcerative colitis, in a subject in need of such treatment, which method comprises administering to said subject a therapeutically-effective amount of a compound according to claim 3.

* * * * *